United States Patent [19]

Izumi et al.

[11] 4,205,182

[45] May 27, 1980

[54] PROCESS FOR PREPARING ETHYL ESTERS OF ALIPHATIC CARBOXYLIC ACIDS

[75] Inventors: Yusuke Izumi, Shinnanyo; Junji Maekawa, Kudamatsu; Katsumi Suzuki, Tokuyama, all of Japan

[73] Assignee: Celanese Corporation, New York, N.Y.

[21] Appl. No.: 945,666

[22] Filed: Sep. 25, 1978

[30] Foreign Application Priority Data

Sep. 28, 1977 [JP] Japan .................................. 52/115540

[51] Int. Cl.$^2$ ........................... C07C 67/04; B01J 21/02
[52] U.S. Cl. ..................................... 560/247; 252/432; 252/437; 252/439; 252/469; 252/470; 252/467
[58] Field of Search ........................................ 560/247

[56] References Cited

U.S. PATENT DOCUMENTS

| | | | |
|---|---|---|---|
| 2,174,985 | 10/1939 | Lazier | 560/247 |
| 2,702,232 | 2/1955 | Arnold | 560/247 |
| 3,644,497 | 2/1972 | Mesich | 560/247 |

*Primary Examiner*—James O. Thomas, Jr.
*Assistant Examiner*—Michael L. Shippen
*Attorney, Agent, or Firm*—Linn I. Grim

[57] ABSTRACT

In a process for producing an ethyl ester of an aliphatic carboxylic acid which comprises reacting ethylene with the aliphatic carboxylic acid in the liquid phase in the presence of an acid catalyst, the improvement wherein a heteropolyacid of tungsten or an acidic metal salt thereof is used as the acid catalyst, and the reaction is carried out in the presence of water in an amount of up to 7.5% by weight based on the weight of the aliphatic carboxylic acid.

27 Claims, No Drawings

PROCESS FOR PREPARING ETHYL ESTERS OF ALIPHATIC CARBOXYLIC ACIDS

This invention relates to a new and improved process for preparing ethyl esters of aliphatic carboxylic acids. More specifically, the invention relates to a process for producing ethyl esters of aliphatic carboxylic acids in one step with high conversions and selectivities by reacting ethylene directly with an aliphatic carboxylic acid in the liquid phase in the presence of a specified acid catalyst.

Methods have been known which afford ethyl esters of aliphatic carboxylic acids by direct reaction of ethylene with aliphatic carboxylic acids in the vapor or liquid phase in the presence of an acid catalyst.

An example of the vapor-phase method is found, for example, in Y. Murakami, H. Uchida and T. Hattori, J. Chem. Soc. Japan, Ind. Chem. Sect. (Kogyo Kagaku Zassi), 72 (9), 1945–1948 (1969) in which the authors discussed the activities of several catalysts including a porous ion exchange resin (Amberlyst 15, a product of Rohm & Haas Co.), silicotungstic acid-silica gel, phosphoric acid-diatomaceous earth and a gel-form ion exchange resin (Amberlite IR-120, a product of Rohm & Haas Co.) in the direct synthesis of ethyl acetate from ethylene and acetic acid by an atmospheric pressure vapor-phase circulating method. Japanese Laid-Open Patent Publication No. 48617/77 discloses a process for producing ethyl acetate by reacting ethylene with acetic acid in the vapor phase in the presence of an acid catalyst comprising silicon dioxide having a surface area of 50 to 200 m$^2$/g obtained by dipping it in sulfuric acid, diethyl sulfate, ethyl sulfate or a mixture thereof. The Murkami et al. article reports that the porous ion exchange resin catalyst has the highest activity among the catalysts tested. However, this ion exchange resin has the defect of being unstable to high temperatures required for the reaction. The silicotungstic acid-silica gel determined to have the second highest activity is not feasible because in a vapor-phase method, its activity is reduced drastically with time. In the vapor-phase method described in the above-cited Japanese Laid-Open Patent Publication, a considerable improvement can be achieved in the yield of ethyl acetate, but still with fairly large amounts of by-products, and the method is not entirely satisfactory.

An example of the liquid-phase method is shown in R. D. Morin and A. E. Bearse, Ind. Eng. Chem., 43 (7), 1596–1600 (1951) which reports the direct preparation of esters by reacting lower olefins with organic carboxylic acids in the presence of a mixed catalyst comprising boron fluoride and hydrogen fluoride. This method, however, suffers from the serious disadvantage of heavy reactor corrosion by the catalyst, and also has the defect that it requires a large amount of the catalyst and the life of the catalyst is short. Hence, it has not gained commercial acceptance to date.

U.S. Pat. No. 3,644,497 discloses a process which comprises reacting an ethylenically unsaturated compound and a carboxylic acid in the liquid phase in the presence of a free heteropolyacid to afford the corresponding ester as a main product when the liquid phase is anhydrous, or a mixture of the corresponding ester and alcohol when the liquid phase contains water. The patent, however, states in column 2, lines 24 to 25 that ethylene is one notable exception as it is usually converted to butane-2-ol or the corresponding ester. This shows that the reaction of ethylene as the ethylenically unsaturated compound with a carboxylic acid in the presence of a free heteropolyacid is an exception, and does not afford the corresponding ethyl ester of carboxylic acid. Accordingly, the U.S. Patent teaches that the method of the U.S. Patent cannot be applied to the production of an ethyl ester of a carboxylic acid.

The U.S. Patent suggests the use of heteropolyacids of molybdenum or tungsten as the heteropolyacids, but the working Examples given in this Patent cover the use of only heteropolymolybdic acid. Experiments of the present inventors have shown however, that heteropolymolybdic acid does not give an ethyl ester of a carboxylic acid irrespective of the presence or absence of water.

It has now been found quite unexpectedly from the aforesaid teaching of U.S. Pat. No. 3,644,497 that when a heteropolyacid of tungsten is used together with a certain small amount of water, an ethyl ester of an aliphatic carboxylic acid can be produced at high conversions and selectivities from ethylene and the aliphatic carboxylic acid.

It is an object of this invention therefore to provide a process for producing an ethyl ester of an aliphatic carboxylic acid by the direct esterification reaction of ethylene and the aliphatic carboxylic acid in the liquid phase.

Another object of this invention is to produce an ethyl ester of an alihhatic carboxylic acid in high conversions and selectivities with the inhibition of by-product formation by directly reacting ethylene with the aliphatic carboxylic acid in the liquid phase.

Other objects and advantages of the invention will become apparent from the following detailed description.

According to this invention, there is provided an improved process for producing an ethyl ester of an aliphatic carboxylic acid which comprises reacting ethylene with the aliphatic carboxylic acid in the liquid phase in the presence of an acid catalyst; wherein a heteropolyacid of tungsten or an acidic metal salt thereof is used as the acid catalyst, and the reaction is carried out in the presence of water in an amount of up to 7.5% by weight based on the weight of the aliphatic carboxylic acid.

In the process of the invention, a heteropolyacid of tungsten is used as the acid catalyst in the direct esterification reaction of ethylene with an aliphatic carboxylic acid in the liquid phase. The heteropolyacid of tungsten has a structure in which a certain metal is located as a central atom and a polyacid group of tungsten is coordinated with it. In this compound, the ratio of the number of tungsten atoms to that of the central atoms may vary widely but will generally be between 6:1 and 12:1, especially between 9:1 and 11:1. A number of elements are known such as central atoms. In the present invention, silicon, phosphorus, boron, arsenic, germanium, titanium, cobalt, iron, aluminum, chromium, zirconium, gallium and tellurium are generally used as the central atoms. Among them, silicon, phosphorus and boron, above all silicon, are preferred. Examples of the heteropolyacids of tungsten are listed below.

12-Tungstosilicic acid $H_4[SiW_{12}O_{40}]$,
dimeric 6-tungstophosphoric acid $H_6[P_2W_{12}O_{32}]$,
12-tungstophosphoric acid $H_3[PW_{12}O_{40}]$,
12-tungstoboric acid $H_5[BW_{12}O_{40}]$,
11-tungstoaluminic acid $H_{10}[Al_2W_{22}O_{74}]$,
12-tungstotelluric acid $H_4[TeW_{12}O_{40}]$, and vanadotungstoselenic acid $H_6SeO_2.10WO_3.V_2O_5$.

Among them, tungstosilicic acid, tungstophosphoric acid, and tungstoboric acid, especially the tungstosilicic acid, are especially suitable.

In the presence invention, acidic metal salts of these heteropolyacids of tungsten can also be used. The term "acidic metal salts" denotes a product resulting from substituting at least one alkali or alkaline earth metal or other metal for some of the hydrogen atoms contained in a free heteropolyacid. Suitable acidic metal salts are acidic alkali metal salts such as acidic lithium salts $Li_yH_{4-y}[SiW_{12}O_{40}]$, acidic sodium salts $Na_yH_{4-y}[SiW_{12}O_{40}]$, acidic potassium salts $K_yH_{4-y}[SiW_{12}O_{40}]$ (y being 1, 2 or 3), and acidic copper salt ($CuH_2[SiW_{12}O_{40}]$). The free heteropolyacids are advantageous over the acidic metal salts in the process of this invention.

Since the heteropolyacids of tungsten used as an acid catalyst in the process of the invention are generally decomposed by strongly basic solution, the process should generally be carried out such that the pH of the reaction mixture remains below about 7.0.

The amount of the heteropolyacid of tungsten or its salt is not critical, but generally, it is at least about 3 g per liter of the aliphatic carboxylic acid used. There is no strict upper limit to the amount of the catalyst. But even when it is used in an amount more than necessary, no corresponding advantage can be obtained, but rather the selectivity will possibly be reduced. Generally, the suitable amount of the catalyst is at most about 100 g per liter of the aliphatic carboxylic acid. Especially advantageously, the catalyst is used in an amount of preferably about 5 to about 80 g, more preferably 10 to 70 g, per liter of the aliphatic carboxylic acid.

Another essential feature of the process of this invention is that the reaction should be carried out in the presence of up to 7.5% by weight, based on the weight of the aliphatic carboxylic acid, of water in addition to the acid catalyst. The investigations of the present inventors have shown that when a heteropolyacid of molybdenum described in the working Examples of the above-cited U.S. Pat. No. 3,644,497 is used in the direct esterification reaction of ethylene with an aliphatic carboxylic acid in the liquid phase, the desired ethyl ester of the aliphatic carboxylic acid cannot substantially be formed whether it is carried out in the presence or absence of water; that even when a heteropolyacid of tungsten is used as the acid catalyst, the ethyl ester is not substantially formed or formed only in an extremely low yield if the anhydrous conditions are used or a large quantity of water is used; and that in contrast, when up to 7.5% by weight, based on the weight of the aliphatic carboxylic acid, of water is used in addition to the heteropolyacid of tungsten, the desired ethyl ester can be obtained in high conversions and selectivities.

Thus, one important feature of the esterification reaction in accordance with this invention is that it is carried out in the presence of water in an amount of up to 7.5% by weight based on the weight of the aliphatic carboxylic acid. The mechanism by which the ethyl ester can be formed in good yield by using a specified small amount of water in combination with the heteropolyacid of tungsten is not known. It is theorized however that the water acts as a promotor for the heteropolyacid, and simultaneously as a solvent for the ionization and dissolving of the heteropolyacid.

Accordingly, when the amount of water is too small, no sufficient effect can be exhibited. The lower limit to the amount of water can be set at 0.01% by weight based on the weight of the aliphatic carboxylic acid. It is advantageous that the water is used in an amount of usually from 0.01 to 5.0% by weight, especially from 0.1 to 4.0% by weight, based on the weight of the aliphatic carboxylic acid. The optimum amount of water, however, varies depending upon the type of the aliphatic carboxylic acid used. For example, when acetic acid is used as the carboxylic acid, water is best used in an amount of 1.0 to 3.5% by weight based on the weight of acetic acid. When formic acid, propionic acid, butyric acid and acrylic acid are used as the carboxylic acid, the optimum amounts of water are 0.2 to 3% by weight, 0.03 to 0.3% by weight, 0.05 to 0.5% by weight, and 0.05 to 0.2% by weight, respectively, based on the weight of the respective carboxylic acid.

When water is adhering to the heteropolyacid of tungsten or its acidic metal salt used as a catalyst or it contains water of crystallization, or the ethylene and/or carboxylic acid as reactants contain water, such water should also be considered, and the total amount of water that can be present in the reaction system should be adjusted within the above-specified range. Conveniently, therefore, the catalyst and reactants are fully dried and fed into a reactor in a substantially anhydrous condition, and the required amount of water is fed separately.

Practically any aliphatic carboxylic acids including monocarboxylic acids, dicarboxylic acids, etc. which may be substituted by a halogen atom, or by a hydroxyl, nitro, amino, sulfo, carbonyl or alkoxy group can be used as the aliphatic carboxylic acid in the process of this invention. Examples include formic acid, acetic acid, propionic acid, valeric acid, acrylic acid, chloroacetic acid, adipic acid, succinic acid, butyric acid, caproic acid, n-undecylic acid, palmitic acid, stearic acid, oleic acid, oxalic acid, azelaic acid, glycolic acid, malic acid, and levulinic acid. Suitable aliphatic carboxylic acids are saturated or unsaturated aliphatic monocarboxylic acids containing up to 20 carbon atoms, especially 1 to 5 carbon atoms, typically formic acid, acetic acid, propionic acid, butyric acid and acrylic acid. Among these, acetic acid can be used especially advantageously.

The direct esterification of the carboxylic acid with ethylene can be effected in accordance with a known liquid phase method. Usually, therefore, the reaction is carried out in the substantial absence of solvent. The reaction temperature is not critical, and can be varied over a wide range according to the type of the carboxylic acid used, the type of the catalyst used, etc. The suitable reaction temperature is generally about 130° to about 300° C., preferably about 170° to about 260° C., most preferably about 180° to about 240° C.

The reaction pressure is the one sufficient to maintain at least the reaction system in the liquid phase under the aforesaid reaction temperature conditions. The suitable range of pressure varies according to the amount of ethylene fed, but generally, is at least 50 kg/cm², preferably 100 to 300 kg/cm².

The ratio of ethylene to the aliphatic carboxylic acid is not critical, and can be varied over a wide range depending upon the type of the carboxylic acid, etc. Generally, ethylene can be used in an amount of at least 0.2 mol per mole of the aliphatic carboxylic acid. It has been found in accordance with this invention that the mole ratio of ethylene fed to the aliphatic carboxylic acid considerably affects the yield of the desired ethyl ester, and especially advantageous results can be obtained when ethylene is used in an amount of 0.4 to 1.5 moles, especially 0.5 to 1.0 mole, per mole of the aliphatic carboxylic acid.

The reaction can be performed for about 0.5 to about 10 hours under the above reaction conditions.

The reaction can be performed either continuously, intermittently, or batchwise. The reactants can be added in any desired order. Stirring of the reactants is not always necessary, but can promotes intimate contact between the reactants and can shorten the time required for completing the reaction.

Usually, the reaction in accordance with this invention can be performed in a pressure reactor which is resistant to corrosive attack by the aliphatic carboxylic acid. An anion of the heteropolyacid of tungsten as an acid catalyst tends to decompose on contact with a heavy metal ion such as iron, nickel, or chromium. Desirably, the material of the reactor should not release such a metal ion in addition to being pressure resistant and acid resistant. The suitable material for the reactor is a metallic material selected from titanium, titanium alloys (known titanium alloys containing 0.1 to 2% by weight of nickel, palladium, etc.), zirconium, tantalum, silver and platinum. From the commercial standpoint, titanium or titanium alloys are most suitable.

Quite unexpectedly from the teaching of the above-cited U.S. Pat. No. 3,644,497, the process of this invention can afford an ethyl ester of an aliphatic carboxylic acid in high conversions and selectivities by the direct esterification reaction of ethylene and the aliphatic carboxylic acid in the liquid phase.

Separation of the ethyl ester from the reaction mixture and its purification can be performed by usual methods, for example by using a tray-type distillation tower, or a porous plate-type distillation tower.

The ethyl esters of aliphatic carboxylic acids so obtained can be used in a wide range of applications, for example as solvents for paints and inks, raw materials for organic syntheses, perfumes, and textile modifiers.

The following Examples illustrate the present invention more specifically.

EXAMPLE 1

A 800 ml autoclave equipped with an electromagnetically operated stirrer and having a resistance to a pressure of up to 500 kg/cm$^2$ was charged with 300 ml (5.25 moles) of dehydrated and purified acetic acid, 10 g/l (based on the acetic acid) of tungstosilicic acid as a catalyst, and water in each of the amounts indicated in Table 1 based on acetic acid. Then, with stirring, ethylene was introduced to a pressure of 50 kg/cm$^2$, and 4.2 moles of its was caused to be absorbed.

The reaction temperature was then raised to 210° C. by means of a heating oven, and ethylene was reacted with acetic acid for 3 hours. After the reaction, the reaction mixture was cooled to room temperature. The unreacted ethylene was purged, and the remainder was analyzed by gas chromatography.

From the results of analysis of the reaction mixture in each run, the composition of the product, the yield of ethyl acetate based on the charged acetic acid, and the selectivity of ethyl acetate were determined. The results are shown in Table 1.

Table 1

| Run No. | Reaction conditions | | Composition of the product (mole. %) | | | | | Yield of ethyl acetate (mole %) | Selectivity of ethyl acetate (%) |
|---|---|---|---|---|---|---|---|---|---|
| | Water (wt. %) | Pressure (kg/cm$^2$) | Ethyl acetate | Acetate | Sec.-butyl acetate | Diethyl ether | Ethyl alcohol | | |
| 1-1 | 1.0 | 230 | 15.2 | 0.05 | 0.03 | 0.09 | — | 15.2 | 98.9 |
| 1-2 | 1.3 | 236 | 24.3 | 0.06 | 0.04 | 0.14 | — | 24.3 | 99.0 |
| 1-3 | 1.5 | 215 | 37.5 | 0.06 | 0.06 | 0.25 | 0.06 | 37.6 | 98.9 |
| 1-4 | 1.8 | 207 | 38.5 | 0.07 | 0.06 | 0.20 | — | 38.6 | 99.2 |
| 1-5 | 2.0 | 235 | 36.2 | 0.06 | 0.05 | 0.26 | — | 36.3 | 99.0 |
| 1-6 | 2.5 | 206 | 31.0 | 0.03 | 0.04 | 0.15 | — | 31.0 | 99.3 |
| 1-7 | 3.0 | 165 | 25.2 | 0.06 | 0.05 | 0.13 | — | 25.2 | 99.1 |
| 1-8 | 4.0 | 169 | 16.4 | 0.05 | 0.03 | 0.09 | — | 16.4 | 99.0 |
| 1-9 | 5.0 | 170 | 11.7 | 0.01 | 0.07 | 0.01 | — | 11.7 | 99.2 |
| 1-10 | 7.0 | 168 | 7.2 | 0.03 | 0.07 | 0.01 | — | 7.2 | 98.5 |

EXAMPLE 2

Using the same reactor as used in Example 1, acetic acid and ethylene were reacted under the same conditions as in Example 1 except that the amount of the tungstosilicic acid catalyst was changed to 20 g/l, and water was added in each of the amounts indicated in Table 2. The results are shown in Table 2.

Table 2

| Run No. | Reaction conditions | | Composition of the product (mole %) | | | | | Yield of ethyl acetate (mole %) | Selectivity of ethyl acetate (%) |
|---|---|---|---|---|---|---|---|---|---|
| | Water (wt. %) | Pressure (kg/cm$^2$) | Ethyl acetate | Acetone | Sec.-butyl acetate | Diethyl ether | Ethyl alcohol | | |
| 2-1 | 0.1 | 240 | 9.2 | 0.04 | 0.003 | 0.008 | — | 9.2 | 99.4 |
| 2-2 | 1.0 | 255 | 36.5 | 0.04 | 0.049 | 0.026 | — | 36.5 | 99.7 |
| 2-3 | 1.5 | 221 | 58.3 | 0.06 | 0.076 | 0.72 | 0.08 | 58.4 | 98.5 |
| 2-4 | 2.0 | 203 | 51.5 | 0.04 | 0.059 | 0.28 | — | 51.6 | 99.3 |
| 2-5 | 3.0 | 230 | 39.5 | 0.07 | 0.06 | 0.12 | — | 39.5 | 99.4 |
| 2-6 | 4.0 | 248 | 30.6 | 0.03 | 0.04 | 0.15 | — | 30.6 | 99.3 |
| 2-7 | 5.0 | 255 | 24.7 | 0.06 | 0.05 | 0.13 | — | 24.7 | 99.0 |
| 2-8 | 7.0 | 245 | 15.0 | 0.07 | 0.07 | 0.15 | 0.05 | 15.0 | 97.8 |
| 2-9 | 10.0 | 240 | 10.1 | 0.06 | 0.08 | 0.16 | 0.15 | 10.1 | 95.7 |

EXAMPLE 3

Acetic acid and ethylene were reacted for 1.5 hours under the same conditions as in Example 1 except that the amount of water was adjusted to 1.0% by weight, and the amount of the tungstosilicic acid catalyst was changed to 40 g/l and 60 g/l, respectively. The results are shown in Table 3.

Table 3

| Run No. | Reaction conditions | | Composition of the product (mole %) | | | | | Yield of ethyl acetate (mole %) | Selectivity of ethyl acetate (%) |
|---|---|---|---|---|---|---|---|---|---|
| | Catalyst (g/l) | Pressure (kg/cm$^2$) | Ethyl acetate | Acetone | Sec.-butyl acetate | Diethyl ether | Ethyl alcohol | | |
| 3-1 | 40 | 181 | 43.2 | 0.07 | 0.07 | 0.22 | — | 43.2 | 99.2 |
| 3-2 | 60 | 240 | 61.0 | 0.08 | 0.08 | 0.08 | 0.75 | 61.4 | 96.5 |

EXAMPLE 4

Acetic acid and ethylene were reacted under the same conditions as in Example 2 except that the reaction temperature was changed to 195° C. and the amount of water was changed as shown in Table 4. The results are shown in Table 4.

Table 4

| Run No. | Reaction conditions | | Composition of the product (mole %) | | | | | Yield of ethyl acetate (mole %) | Selectivity of ethyl acetate (%) |
|---|---|---|---|---|---|---|---|---|---|
| | Water (wt. %) | Pressure (kg/cm²) | Ethyl acetate | Acetone | Sec.-butyl acetate | Diethyl ether | Ethyl acetate | | |
| 4-1 | 1.0 | 142 | 10.2 | 0.04 | 0.02 | — | — | 10.2 | 99.4 |
| 4-2 | 1.4 | 148 | 25.0 | 0.06 | 0.05 | 0.13 | — | 25.0 | 99.0 |
| 4-3 | 1.6 | 132 | 28.3 | 0.04 | 0.05 | 0.15 | — | 28.3 | 99.2 |
| 4-4 | 2.0 | 133 | 20.6 | 0.05 | 0.02 | 0.09 | — | 20.6 | 99.2 |
| 4-5 | 3.0 | 132 | 16.1 | 0.05 | 0.03 | 0.09 | — | 16.1 | 98.9 |
| 4-6 | 5.0 | 150 | 10.4 | 0.05 | 0.06 | — | — | 10.4 | 98.9 |
| 4-7 | 7.0 | 140 | 5.2 | 0.07 | 0.08 | — | — | 5.2 | 97.2 |
| 4-8 | 10.0 | 113 | 2.0 | 0.05 | 0.09 | — | — | 2.0 | 91.5 |

EXAMPLE 5

Acetic acid and ethylene were reacted under the same conditions as in Example 2 except that the reaction temperature was changed to 180° C. and the amount of water was changed as shown in Table 5. The results are shown in Table 5.

Table 5

| Run No. | Reaction conditions | | Composition of the product (mole %) | | | | | Yield of ethyl acetate (mole %) | Selectivity of ethyl acetate (%) |
|---|---|---|---|---|---|---|---|---|---|
| | Water (wt. %) | Pressure (kg/cm²) | Ethyl acetate | Acetone | Sec.-butyl acetate | Diethyl ether | Ethyl acetate | | |
| 5-1 | 1.0 | 150 | 4.3 | 0.04 | 0.03 | 0.008 | — | 4.3 | 98.2 |
| 5-2 | 1.5 | 146 | 17.8 | 0.08 | 0.06 | 0.02 | — | 17.8 | 99.1 |
| 5-3 | 2.5 | 150 | 9.8 | 0.04 | 0.06 | 0.02 | — | 9.8 | 98.8 |

EXAMPLE 6

Acetic acid and ethylene were reacted under the same conditions as in Example 2 except that the reaction temperature was changed to 230° C. and the amount of water was changed as shown in Table 6. The results are shown in Table 6.

Table 6

| Run No. | Reaction conditions | | Composition of the product (mole %) | | | | | Yield of ethyl acetate (mole %) | Selectivity of ethyl acetate (%) |
|---|---|---|---|---|---|---|---|---|---|
| | Water (wt. %) | Pressure (kg/cm²) | Ethyl acetate | Acetone | Sec.-butyl acetate | Diethyl ether | Ethyl alcohol | | |
| 6-1 | 1.0 | 325 | 42.3 | 0.07 | 0.10 | 2.2 | 0.5 | 43.3 | 93.6 |
| 6-2 | 1.5 | 320 | 70.5 | 0.08 | 0.12 | 3.8 | 0.8 | 73.8 | 93.6 |
| 6-3 | 3.0 | 315 | 45.2 | 0.07 | 0.08 | 2.0 | 0.5 | 46.3 | 94.5 |
| 6-4 | 5.0 | 310 | 32.1 | 0.06 | 0.07 | 1.8 | 0.2 | 32.7 | 93.8 |

EXAMPLE 7

The same procedure as in Example 1 was repeated except that the amount of water was changed to 1.5% by weight, and the pressure of ethylene fed was changed as shown in Table 7 (that is, the mole ratio of ethylene to acetic acid was changed). The results are shown in Table 7.

Table 7

| Run No. | Reaction conditions | | | Composition of the product (mole %) | | | | | Yield of ethyl acetate (mole %) | Selectivity of ethyl acetate (%) |
|---|---|---|---|---|---|---|---|---|---|---|
| | Pressure of ethylene fed (kg/cm²) | Ethylene (mole) | Pressure (kg/cm²) | Ethyl acetate | Acetone | Sec.-Butyl acetate | Diethyl ether | Ethyl alcohol | | |
| 7-1 | 30 | 1.7 | 50 | 2.8 | 0.01 | 0.01 | — | — | 2.8 | 99.3 |
| 7-2 | 40 | 2.5 | 100 | 7.9 | 0.04 | 0.01 | — | — | 7.9 | 99.4 |
| 7-3 | 45 | 3.2 | 180 | 23.6 | 0.06 | 0.06 | 0.02 | — | 23.6 | 99.4 |
| 7-4 | 50 | 4.1 | 270 | 29.6 | 0.04 | 0.06 | 0.03 | — | 29.6 | 99.5 |
| 7-5 | 55 | 5.8 | 350 | 31.0 | 0.05 | 0.06 | 0.06 | — | 31.0 | 99.4 |

EXAMPLE 8

Acetic acid and ethylene were reacted under the same conditions as in Example 2 except that the amount of water was maintained constant at 1.5% by weight, and 20 g/l (based on acetic acid) of each of the heteropolyacid of tungsten and its acidic metal salts shown in Table 8 was used instead of tungstosilicic acid. The results are shown in Table 8.

Table 8

| Run No. | Type of catalyst | Reaction conditions Pressure (kg/cm²) | Composition of the product (mole %) | | | | | Yield of ethyl acetate (mole %) | Selectivity of ethyl acetate (%) |
|---|---|---|---|---|---|---|---|---|---|
| | | | Ethyl acetate | Acetone | Sec.-Butyl acetate | Diethyl ether | Ethyl alcohol | | |
| 8-1 | Tungstophosphoric acid | 220 | 12.0 | 0.07 | 0.15 | 0.03 | — | 12.0 | 97.9 |
| 8-2 | Tungsto- | 235 | 7.5 | 0.05 | 0.10 | 0.03 | — | 7.5 | 97.6 |

Table 8-continued

| Run No. | Reaction conditions Type of catalyst | Pressure (kg/cm²) | Composition of the product (mole %) Ethyl acetate | Acetone | Sec.-Butyl acetate | Diethyl ether | Ethyl alcohol | Yield of ethyl acetate (mole %) | Selectivity of ethyl acetate (%) |
|---|---|---|---|---|---|---|---|---|---|
| 8-3 | boric acid NaH₃SW[a] | 205 | 25.0 | 0.07 | 0.05 | 0.05 | — | 25.0 | 99.3 |
| 8-4 | Na₂H₂SW[b] | 209 | 18.1 | 0.05 | 0.03 | 0.01 | — | 18.1 | 99.5 |
| 8-5 | CuH₂SW[c] | 215 | 15.5 | 0.03 | 0.02 | 0.01 | — | 15.5 | 99.6 |

Note
[a] NaH₃SW is an abbreviation of NaH₃[SiW₁₂O₄₀].
[b] Na₂H₂SW is an abbreviation for Na₂H₂[SiW₁₂O₄₀].
[c] CuH₂SW is an abbreviation for CuH₂[SiW₁₂O₄₀].

EXAMPLE 9

The same reactor as used in Example 1 was charged with 300 ml (7.9 moles) of dehydrated and purified formic acid and 20 g/l (based on formic acid) of tungstosilicic acid as a catalyst and water in the amount shown in Table 9 based on the formic acid. Then, with stirring, ethylene was introduced to a pressure of 50 kg/cm², and 2.4 moles of it was caused to be absorbed.

Then, the reaction temperature was raised to 180° C. by means of a heating oven, and formic acid and ethylene were reacted for 3 hours.

After the reaction, the reaction mixture was treated in the same way as in Example 1 and analyzed.

The results in each run are shown in Table 9.

Table 9

| Run No. | Reaction conditions Water (wt. %) | Pressure (kg/cm²) | Composition of the product (wt. %) Ethyl formate | Butyl formate | Others | Yield of ethyl formate (mole %) | Selectivity of ethyl formate (%) |
|---|---|---|---|---|---|---|---|
| 9-1 | 0.2 | 170 | 3.5 | 0.4 | 1.5 | 3.5 | 64.8 |
| 9-2 | 0.8 | 165 | 10.8 | 0.3 | 0.9 | 10.8 | 90.0 |
| 9-3 | 2.4 | 168 | 7.5 | 0.3 | 0.7 | 7.5 | 88.3 |

EXAMPLE 10

The same reactor as used in Example 1 was charged with 300 ml (3.2 moles) of dehydrated and purified propionic acid, 20 g/l (based on propionic acid) of tungstosilicic acid as a catalyst and water in each of the amounts indicated in Table 10 based on propionic acid. With stirring, ethylene was introduced to a pressure of 45 kg/cm², and 4.2 moles of it was caused to be absorbed. As a reaction temperature of 180° C., propionic acid and ethylene were reacted for 3 hours.

The results in each run are shown in Table 10.

Table 10

| Run No. | Reaction conditions Water (wt. %) | Pressure (kg/cm²) | Composition of the product (mole %) Ethyl propionate | Sec.-Butyl propionate | Others | Yield of ethyl propionate (mol %) | Selectivity of ethyl propionate (%) |
|---|---|---|---|---|---|---|---|
| 10-1 | 0.04 | 104 | 5.1 | 0.07 | 0.5 | 5.1 | 89.9 |
| 10-2 | 0.10 | 101 | 13.3 | 0.10 | 0.6 | 13.3 | 95.0 |
| 10-3 | 0.20 | 108 | 30.1 | 0.13 | 0.8 | 30.1 | 97.0 |
| 10-4 | 0.28 | 99 | 14.2 | 0.11 | 0.7 | 14.2 | 94.6 |
| 10-5 | 1.00 | 105 | 2.2 | 0.03 | 0.5 | 2.2 | 80.6 |
| 10-6 | 5.00 | 104 | 1.4 | 0.03 | 0.3 | 1.4 | 80.9 |

EXAMPLE 11

The same reactor as used in Example 1 was charged with 300 ml (3.4 moles) of dehydrated and purified butyric acid, 20 g/l (based on butyric acid) of tungstosilicic acid, and water in each of the amounts indicated in Table 11 based on butyric acid. With stirring, ethylene was introduced to a pressure of 50 kg/cm², and 4.0 moles of it was caused to be absorbed. The reaction temperature was then adjusted to 180° C., and butyric acid and ethylene were reacted for 3 hours.

The results are shown in Table 11.

Table 11

| Run No. | Reaction conditions Water (wt. %) | Pressure (kg/cm²) | Composition of the product (mole %) Ethyl butyrate | Butyl butyrate | Others | Yield of ethyl butyrate (mole %) | Selectivity of ethyl butyrate (%) |
|---|---|---|---|---|---|---|---|
| 11-1 | 0.2 | 157 | 25.0 | 0.2 | 0.8 | 25.0 | 96.1 |
| 11-2 | 1.0 | 160 | 0.5 | 0.05 | 0.1 | 0.5 | 76.9 |

EXAMPLE 12

The same reactor as used in Example 1 was charged with 300 ml (4.4 moles) of dehydrated and purified acrylic acid, 2 g/l of hydroquinone as a polymerization inhibitor, 20 g/l (based on acrylic acid) of tungstosilicic acid as a catalyst, and water in each of the amounts shown in Table 12 based on acrylic acid. With stirring, ethylene was introduced to a pressure of 45 kg/cm², and 2.9 moles of it was caused to be absorbed. Then, the reaction temperature was adjusted to 150° C., and acrylic acid and ethylene were reacted for 3 hours.

The results are shown in Table 12.

Table 12

| Run No. | Reaction conditions Water (wt. %) | Pressure (kg/cm²) | Composition of the product (mole %) Ethyl acrylate | others | Yield of ethyl acrylate (mole %) | Selectivity of ethyl acrylate (%) |
|---|---|---|---|---|---|---|
| 12-1 | 0.1 | 110 | 5.3 | 1.2 | 5.3 | 81.5 |
| 12-2 | 0.5 | 107 | 1.6 | 0.3 | 1.6 | 83.8 |

EXAMPLE 13

The same reactor as in Example 1 was charged with 300 ml (5.25 moles) of dehydrated and purified acetic acid, 6 g of dried tungstosilicic acid as a catalyst and 4.8 g of water. With stirring, ethylene was introduced to a pressure of 50 kg/cm². The reaction temperature was raised to 210° C. (pressure 230 kg/cm²), acetic acid and ethylene were reacted for 3 hours. After the reaction, the pressure of the inside of the reactor was 55 kg/cm².

Immediately after the reaction, the reaction mixture was cooled to room temperature. Then, the unreacted ethylene was purged, and 480 ml of the reaction mixture was taken out. A part of the reaction mixture was analyzed by gas chromatography. The results are shown in Table 13 as those of the first reaction.

Then, the entire reaction mixture was distilled by an Oldershow-type 30-tray glass distillation tower to separate low-boiling substances, water and ethyl acetate from the top of the tower. The distillation was continued until ethyl acetate was hardly present in the still residue. To 120 ml of the resulting still residue 180 ml of acetic acid and 4.8 g of water were freshly added, and the reaction was performed under the same conditions and by the same operation as in the first reaction. The results are given in Table 13 as those of the second reaction.

In a similar manner, the third to the fifth reactions were performed. The results are shown in Table 13.

Table 13

| Cycle of the reaction | Reaction pressure (kg/cm²) | Composition of the product (mole %) | | | | | Yield of ethyl acetate (mole %) | Selectivity of ethyl acetate (%) |
|---|---|---|---|---|---|---|---|---|
| | | Ethyl acetate | Acetone | Sec.-Butyl Alcohol | Diethyl ether | Ethyl alcohol | | |
| 1st | 230 | 58.0 | 0.06 | 0.07 | 0.72 | 0.08 | 58.4 | 98.3 |
| 2nd | 228 | 57.8 | 0.07 | 0.07 | 0.61 | 0.09 | 58.1 | 98.5 |
| 3rd | 235 | 55.5 | 0.07 | 0.06 | 0.75 | 0.07 | 55.9 | 98.3 |
| 4th | 240 | 56.7 | 0.08 | 0.08 | 0.83 | 0.09 | 57.1 | 98.1 |
| 5th | 235 | 57.8 | 0.08 | 0.09 | 0.70 | 0.08 | 58.2 | 98.2 |

From the results obtained by repeatedly using the tungstosilicic catalyst, it was found that the activity of the catalyst was very stable.

We claim:

1. In a process for producing an ethyl ester of an aliphatic carboxylic acid which comprises reacting ethylene with an aliphatic carboxylic acid in the liquid phase in the presence of an acid catalyst, the improvement wherein the acid catalyst used is a heteropolyacid of tungsten or its acid metal salt selected from the group consisting of acidic alkali metal salts and acidic copper salt, said heteropolyacid having a central atom of silicon, phosphorus, boron, arsenic, germanium, titanium, cobalt, iron, aluminum, chromium, zirconium, gallium or tellurium and the reaction is carried out in the presence of water in an amount ranging from about 0.01 to about 7.5% by weight based on the weight of said aliphatic carboxylic acid.

2. The process of claim 1 wherein the heteropolyacid of tungsten is tungstosilicic acid.

3. The process of claim 1 wherein the heteropolyacid of tungsten is tungstoboric acid.

4. The process of claim 1 wherein the heteropolyacid of tungsten is tungstophosphoric acid.

5. The process of claim 1 wherein the heteropolyacid of tungsten is an acid metal salt having the formula:

$$NaH_3[SiW_{12}O_{40}]$$

6. The process of claim 1 wherein the heteropolyacid of tungsten is an acid metal salt having the formula:

$$Na_2H_2[SiW_{12}O_{40}]$$

7. The process of claim 1 wherein the heteropolyacid of tungsten is an acid metal salt having the formula:

$$CuH_2[SiW_{12}O_{40}]$$

8. The process of claim 1 wherein the amount of the heteropolyacid of tungsten and its acidic metal salt ranges from about 3 to about 80 grams per liter of the aliphatic carboxylic acid.

9. The process of claim 8 wherein the amounts of the heteropolyacid of tungsten and its acidic metal salt ranges from about 10 to about 70 grams per liter of the aliphatic carboxylic acid.

10. The process of claim 1 wherein the amount of water ranges from about 0.01 to about 5.0% by weight based on the weight of the aliphatic carboxylic acid.

11. The process of claim 10 wherein the amount of water ranges from about 0.1 to about 3.5% by weight based on the weight of the aliphatic carboxylic acid.

12. The process of claim 1 wherein the reaction is carried out at a temperature in the range from about 130° C. to about 300° C.

13. The process of claim 12 wherein the reaction is carried out at a temperature in the range from about 170° C. to about 240° C.

14. The process of claim 1 wherein the amount of ethylene range from about 0.2 to about 1.5 moles per mole of aliphatic carboxylic acid.

15. The process of claim 14 wherein the amount of ethylene ranges from about 0.4 to about 1.5 moles per mole of the aliphatic carboxylic acid.

16. The process of claim 1 wherein the aliphatic carboxylic acid is an aliphatic monocarboxylic acid having 1 to 5 carbon atoms.

17. The process of claim 16 wherein the aliphatic carboxylic acid is selected from the group consisting of formic acid, acetic acid, propionic acid, butyric acid and acrylic acid.

18. The process of claim 1 for producing ethyl acetate which comprises reacting ethylene with acetic acid in the liquid phase in the presence of a catalyst tungstosilicic acid.

19. The process of claim 18 wherein the catalyst is tungstophosphoric acid.

20. The process of claim 18 wherein the catalyst is tungstoboric acid.

21. The process of claim 18 wherein the catalyst has the formula:

$$NaH_3[SiW_{12}O_{14}]$$

22. The process of claim 18 wherein the catalyst has the formula:

$$Na_2H_2[SiW_{12}O_{40}]$$

23. The process of claim 18 wherein the catalyst has the formula:

$$CuH_2[SiW_{12}O_{40}]$$

24. The process of claim 1 for producing ethyl formate which comprises reacting ethylene with formic acid in the liquid phase in the presence of tungstosilicic acid.

25. The process of claim 1 for producing ethyl propionate which comprises reacting ethylene with propionic acid in the liquid phase in the presence of tungstosilicic acid.

26. The process of claim 1 for producing ethyl butyrate which comprises reacting ethylene with butyric acid in the liquid phase in the presence of tungstosilicic acid.

27. The process of claim 1 for producing ethyl acrylate which comprises reacting ethylene with acrylic acid in the liquid phase in the presence of tungstosilicic acid.

* * * * *